United States Patent [19]

Arai et al.

[11] Patent Number: 4,786,595

[45] Date of Patent: Nov. 22, 1988

[54] ANALYTICAL ELEMENT FOR ANALYSIS OF AN ANALYTE

[75] Inventors: Fuminori Arai; Takushi Miyazako; Harumi Katsuyama, all of Asaka, Japan

[73] Assignee: Fuji Photo Film Co., Ltd., Kanagawa, Japan

[21] Appl. No.: 858,545

[22] Filed: Apr. 29, 1986

Related U.S. Application Data

[63] Continuation of Ser. No. 553,170, Nov. 18, 1983, abandoned.

[30] Foreign Application Priority Data

Nov. 19, 1982 [JP] Japan ................................. 57-202157

[51] Int. Cl.[4] .................... C12Q 1/26; G01N 21/77; G01N 33/546

[52] U.S. Cl. ....................................... 435/25; 422/55; 422/56; 422/57; 422/60; 435/11; 435/12; 435/14; 435/18; 435/22; 436/534; 436/501; 436/805; 436/169; 436/170

[58] Field of Search .................... 422/56, 57, 55, 60; 435/11, 12, 14, 18, 22, 25, 19, 26; 436/533, 534, 805, 169, 170, 501

[56] References Cited

U.S. PATENT DOCUMENTS

| | | | |
|---|---|---|---|
| 3,616,229 | 11/1971 | Wildi et al. | 436/533 X |
| 3,715,325 | 2/1973 | Linoli et al. | 435/19 X |
| 3,953,295 | 4/1976 | Monte et al. | 435/25 X |
| 4,050,898 | 9/1977 | Goffe et al. | 422/57 |
| 4,144,306 | 3/1979 | Figueras | 435/22 X |
| 4,258,001 | 3/1981 | Pierce et al. | 435/805 X |
| 4,430,436 | 2/1984 | Koyama et al. | 436/531 |
| 4,486,537 | 12/1984 | Koyama et al. | 436/170 |

FOREIGN PATENT DOCUMENTS 59-0300 2/1984 Japan..

Primary Examiner—Robert J. Warden
Assistant Examiner—Jack Spiegel
Attorney, Agent, or Firm—Jules E. Goldberg

[57] ABSTRACT

An analytical element for quantitative analysis of analyte contained in a body fluid or the like, which has at least one reagent layer comprising a reactive reagent and a binder, characterized in that a portion or whole of the binder is a polycarboxylic acid carrying a nonionic surface active agent attached through ester linkage to at least a portion of the carboxyl groups contained therein.

8 Claims, 1 Drawing Sheet

ANALYTICAL ELEMENT FOR ANALYSIS OF AN ANALYTE

This is a continuation of application Ser. No. 553,170, filed Nov. 18, 1983 now abandoned.

BACKGROUND OF THE INVENTION

1. Field of the Invention

The present invention relates to an improved analytical element for quantitative analysis of substance contained in aqueous liquids, and particularly contained in body fluids.

2. Description of Prior Arts

A variety of methods for analysis of substance contained in water, foodstuffs and body fluids are heretofore proposed. Particularly a method comprising procedures of promoting formation of colored material in a liquid sample which occurs in proportion to the amount of the substance under analysis (analyte) and measuring the color density is well known in the analysis. This method has been utilized not only in solution analysis (wet analysis) but also in dry analysis. Such dry analysis utilizes, for instance, a dry sheet similar to a pH test strip wherein a paper or other absorbent carrier is impregnated with a reagent for forming color upon contact with an analyte.

Also known is an analytical element sheet or film having single-layer or multi-layer structure for the dry analysis, which is appropriate for quantitative analysis of analyte with high accuracy.

The above-mentioned multilayer analytical element is also termed a multilayer analytical material, and various elements are known. For instance, a multilayer analytical element comprising a support, one or more reagent layers provided thereon and a non-fibrous porous spreading layer provided thereon is disclosed in U.S. Pat. Nos. 3,630,957, 3,992,158, 3,983,005, 4,042,335, 4,069,017, and 4,144,306, and U.S. Pat. Re. No. 30,267, and others.

In the multilayer analytical element, when applied an aqueous liquid sample containing an analyte onto the spreading layer, the aqueous liquid sample permeates the reagent layer maintaining a uniform amount per unit area to produce color formation reaction. After a certain period of time, the color density is measured to determine a concentration analyte in the aqueous liquid sample.

Representative examples of the analytes analyzable by means of the above-described multilayer analytical element include a variety of hydrolase contained in body fluids, such as, blood, urine, intestinal juice, saliva, spinal fluid and pancreatic juice. In addition to the hydrolase, other substances contained in body fluids, such as, cholesterol, triglyceride (neutral fat), glucose and uric acid, which are decomposable by action of oxidoreductase, especially oxidase, to produce a low molecular weight compound and hydrogen peroxide, can be mentioned.

At present, various hydrolases are known. The multilayer analytical element is particularly useful for analysis of hydrolase whose substrate is a high molecular weight compound and which produces a diffusive low molecular weight product through hydrolysis. Quantitative analyses of the hydrolase is important in clinical test, and a simple and accurate analytical method is highly desired. Examples of such hydrolase include amylase, lipase, protease such as trypsin, chymotrypsin and pepsin, pectinase and various kinases.

For instance, measurement of amount of amylase contained in blood is clinically very important for observing conditions of pancreas function. Amylase is one of hydrolases that hydrolyzes amylose linkages of starch or the like and produces a low molecular weight polysaccharide, oligosaccharide or monosaccharide. Amylase is generally analyzed by a method of measuring the enzymic activity and calculating a relative value of its concentration in the liquid sample.

The aforementioned Japanese patent provisional publication No. 53(1978)-131089 describes a dry multilayer analytical element capable of measuring the amylase activity by means of an extremely simple procedure. The multilayer analytical element has a reagent layer comprising a substrate of amylase such as a non-diffusive substrate carrying a detectable chromophore (e.g. starch carrying dye groups), and a registration layer for receiving a diffusive reaction product given by hydrolyzing action of analyte, that is, amylase. In the method of analysis of the amylase activity employing this multilayer analytical element, a non-diffusive substrate carrying a detectable chromophore (dye or the like) is decomposed by action of the amylase contained in a liquid sample to produce a diffusive low molecular weight product having chromophore. The low molecular weight product is diffused in the reagent layer, and finally received and fixed in the registration layer. Then, the amount of the reaction product can be determined by measuring photometrically the color density proportional to the amount of the diffusive low molecular weight product carrying chromophore received by the registration layer.

The aforementioned Japanese patent provisional publication No. 51(1976)-40191 discloses an analytical element having a layer constitution similar to that described in the above-mentioned Japanese patent provisional publication No. 53(1978)-1310899. The former involves procedures of converting originally undetectable chemical species to diffusive and detectable chemical species in a reagent layer under action of analyte, and detecting the chemical species in a detection layer (registration layer), while the latter element contains originally detectable chemical species in a reagent layer.

In these arts, a detection layer or registration layer functions only for receiving a diffusive chemical species, and no color formation reaction takes place therein. Accordingly, in order to clearly distinguish the detectable chemical species remaining in the reagent layer from the chemical species received in the detection layer or registration layer and to obtain quantitative analytical results, a radiation blocking layer having light blocking or shielding characteristics is necessarily provided therebetween for the purpose of color blocking.

Japanese patent provisional publication No. 57(1982)-40649 describes a multilayer analytical element improved in the above-described defect. In the multilayer analytical element, a substrate contained in a substrate layer of the element reacts with analyte to give a substantially colorless diffusive product, and the diffusive product then reacts with a chromogen to form a detectable color. Generally, the chromogen is previously introduced into the multilayer analytical elment in such manner that the chromogen is contained in a color reaction layer attached to the substrate layer. Accordingly, by the use of this multilayer analytical element, the reaction product is easily distinguished from the unreacted substrate.

However, in the case that a diazonium compound is employed in the last-described art as the chromogen which reacts with a diffusive product to form a detectable color, the diazonium compound is unstable and undergoes decomposition reaction and various undesirable side reactions, whereby giving poor quantitative results.

Generally, the diazonium compound is known to be unstable. However, it is also known that the above-described decomposition reaction or various side reactions are reduced by introducing an acid such as citric acid, tartaric acid, phosphoric acid or naphthalenesulfonic acid into a reaction system to lower pH for keeping the system in acidic conditions. In addition, it is further known that an anion originating from zinc chloride, tetrafluoroborate, hexafluoroaluminate and the like can be present as a counter ion of the diazonium compound to stabilize the diazonium compound. Those arts are described in "PHOTOSENSITIVE DIAZO COMPOUND" by M. S. Dinaburg (THE FOCAL PRESS, 1964). In the art, although the diazonium compound is stabilized by the adjustment of pH of reaction system, the so adjusted pH value unfavorably deviates from the optimum pH range of analyte (for instance, around pH 6.9, such as pH 6.5–7.5, for human amylase). Accordingly, the enzymic activity of the analyte does not appropriately function under these conditions, and no reliable analytical result is obtained.

The above-described problem on the stabilization of the diazonium compound has been solved by employing a polycarboxylic acid as binder. It has been then discovered that the stabilization of a diazonium compound is accomplished without disturbing the analytical reaction involved. This invention has been applied for patent in Japanese patent application No. 57(1983)-140736.

SUMMARY OF THE INVENTION

As a result of studies on the above-described art, the present inventors have found a disadvantageous fact that although the stabilization of a diazonium compound is accomplished by the employment of a polycarboxylic acid as binder, unfavorable phenomenon such as precipitation of the diazonium compound occurs in the preparation of an aqueous coating solution containing a diazonium compound and a binder of a polycarboxylic acid, i.e., a polymer containing a great number of carboxylic acid groups in the molecule. The reason is that since the diazonium compound employed is so selected as to have a hydrophobic group for preventing diffusion of the compound from a color reaction layer, the compound shows no sufficient solubility in an aqueous solution of the polycarboxylic acid binder. Moreover, in the preparation of a color reaction layer using the so prepared coating solution, the diazonium compound is apt to separate over the color reaction layer. The color reaction layer having such separated substance lowers the accuracy of the analysis in the use of analytical element.

The present inventors have made further studies for solving the above-described problems and found that replacement of the above-mentioned simple polycarboxylic acid with a polycarboxylic acid (a polymer containing a great number of carboxylic acid groups in the molecule) carrying a nonionic surface active agent which is attached through ester linkage to at least a portion of the carboxyl groups contained in the molecule not only makes it possible to stabilize the diazonium compound, but also improves the solubility of the diazonium compound having a hydrophobic group in the aqueous binder solution. For this reason, disadvantageous phenomenon such as precipitation of the diazonium compound in a coating solution or separation from the resulting layer is effectively obviated.

The present inventors have also found that the polycarboxylic acid carrying a nonionic surface active agent (hereinafter, referred to as "polycarboxylic acid derivative") is not only useful for the improvement of the stability and solubility of the diazonium compound in an aqueous coating solution, but also extremely valuable as a binder to be employed for the preparation of reagent layers of an analytical element comprising various reactive reagents such as a substrate, an enzyme, a dye and a color forming compound which are desirably kept under a low pH condition for maintaining the high stability and activity because the polycarboxylic acid derivative has the high solubilizing power and the function of maintaining the low pH conditions.

Accordingly, the present invention provides an analytical element having at least one reagent layer comprising a reactive reagent and a binder, characterized in that a portion or whole of the binder is a polycarboxylic acid carrying a nonionic surface active agent attached through ester linkage to at least of a portion of the carboxyl groups contained therein.

The analytical element of the invention is generally employed in the form of a multilayer analytical sheet or film comprising a spreading layer, a reagent layer and a support (generally a transparent support) superposed in this order, but the spreading layer and the support are not essential for the analytical element of the present invention.

BRIEF DESCRIPTION OF THE DRAWINGS

Each of FIGS. 1 through 5 shows a sectional view showing a typical structure of a multilayer analytical element embodying the analytical element according to the present invention.

Figure 1:
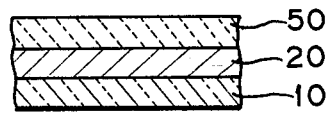
FIG. 1 illustrates a multilayer analytical element composed of a support, a color reaction layer and a coupler substrate layer.

In the figures, numbers means as follows: 10: support, 20: color reaction layer, 30: diffusion-preventive layer, 40: light blocking layer, 50: coupler substrate layer, 60: reagent layer, 61: color reactive phase, 62: coupler substrate phase, 70: spreading layer.

DETAILED DESCRIPTION OF THE INVENTION

Representative examples of the substance to be analyzed, namely analyte, by the use of the analytical element of the invention include hydrolases such as proteases (trypsin, chymotrypsin, pepsin, etc.), amylase, lipase and pectinase. For the analysis of such hydrolase, the analytical element of the present invention preferably is in the form of a multilayer analytical element which comprises a diazonium color reaction layer containing a diazonium compound in a binder and a coupler substrate layer provided on the color reaction layer, in which a portion or whole of the binder is a polycarboxylic acid carrying a nonionic surface active agent attached via ester linkage to at least a portion of carboxyl groups thereof.

The analyte analyzable by the analytical element of the present invention is not restricted to the hydrolase. Other examples of the analyte are substances present in a body fluid, such as cholestrol, triglyceride (neutral fat), glucose and uric acid, which are decomposable by action of oxidoreductase, particularly oxidase, producing hydrogen peroxide and a low molecular weight product. Examples of the oxidoreductase applicable to the above-described substances include oxidases such as cholesterol oxidase for cholesterol, glycerol oxidase for triglyceride, glucose oxidase for glucose, and uricase for uric acid. Oxidase is generally employed in combination with peroxidase. As for the oxidase and peroxidase, the optimum pH range for their enzymic activities is on the acidic side (for instance, approx. pH 5.6 for glucose oxidase, approx. pH 5.8 for cholesterol oxidase and pH 6.7 for peroxidase). Accordingly, in the preparation of an analytical element having a reagent layer containing the oxidase and peroxidase as the reactive reagents, the polycarboxylic acid derivative binder employed in the present invention, that is, a polycarboxylic acid carrying a nonionic surface active agent is attached through ester linkage to at least a portion of carboxyl groups thereof is employed as a whole or a portion of the binder for the reagent layer, whereby giving a reagent layer in which the oxidase and/or peroxidase are homogeneously and stably contained.

It is desired for the polycarboxylic acid derivative binder employable in the invention that a polycarboxylic acid contains a repeating unit of a divalent group derived from a compound having a carboxyl groups and an ethylenic-unsaturated double bond, and the nonionic surface active agent is attached to at least a portion of the carboxyl groups through ester linkage.

In the polycarboxylic acid derivative binder, the divalent group derived from a compound having the repeating unit including the carboxyl group and ethylenic-unsaturated double bond preferably has the formula (I):

The polycarboxylic acid derivative binder employable in the invention can be obtained, for instance, in the following manner. A polycarboxylic acid is initially prepared. The so prepared polycarboxylic acid is caused to react with a nonionic surface active agent having a hydroxyl group in the molecule, optionally in the presence of a catalyst, to perform an esterification reaction between a portion of a great number of the carboxyl groups contained in the polycarboxylic acid and the hydroxyl group of nonionic surface active agent. Through the esterification reaction, a polycarboxylic acid derivative carrying a nonionic surface active agent attached to a portion of the carboxyl groups of the polycarboxylic acid.

Representative examples of the polycarboxylic acid include acrylic acid copolymers, methacrylic acid copolymers, maleic acid copolymers, copolymers of a maleic acid copolymers, copolymers of a maleic acid monoester such as monomethyl maleate, monoethyl maleate, monopropyl maleate, monobutyl maleate and monoamyl maleate, and itaconic acid copolymers and copolymers of itaconic acid monesters such as monomethyl itaconate, monoethyl itaconate, monopropyl itaconate, monobutyl itaconate and monoamyl itaconate.

Examples of comonomers for the above-described copolymers include acrylic acid esters such as methyl acrylate, ethyl acrylate, propyl acrylate, butyl acrylate, pentyl acrylate, amyl acrylate and hydroxyethyl acrylate, alkyl vinyl ethers such as methyl vinyl ether, ethyl vinyl ether, propyl vinyl ether and butyl vinyl ether, styrene, and p-hydroxystyrene.

The polycarboxylic acid derivative generally contains divalent groups derived from a compound having a combination of carboxyl groups and ethylenic-unsaturated double bonds as a repeating unit in the amount of approx. 10–90 mol %, and preferably approx. 30–60 mol %.

The polycarboxylic acid derivative of the present invention may be employed as a binder in combination with other polymers. For instance, the polycarboxylic acid derivative can be employed, if desired, in combination with polymers such as poly(styrenesulfonic acid), poly(2-acrylamido-2-methylpropanesulfonic acid), polyacrylamide, poly(N-vinylpyrrolidone), hydroxyethyl cellulose, hydroxypropyl cellulose, ethyl cellulose, carboxymethyl cellulose and agarose.

There is no specific limitation on the molecular weight of the polycarboxylic acid derivative, as far as the stabilization of the reactive reagent such as a diazonium compound or oxidase can be accomplished without disturbing the reaction between the reactive reagent contained in a reagent layer of the analytical element and an analyte or a decomposition product of the analyte. However, from the viewpoint of physical properties as the binder for the formation of a layer, the polycarboxylic acid derivative has the molecular weight in the range of approx. 30,000–5,000,000, and preferably in the range of approx. 50,000–1,000,000. If the molecular weight of the polycarboxylic acid derivative exceeds the above upper limit, the viscosity is so high that the coating procedure is difficultly done. On the other hand, if the molecular weight is below the lower limit, the viscosity is too low to give an even coating layer. In addition, a reactive reagent such as a diazonium salt is liable to precipitate, and as a result, a uniform color reaction layer can be hardly obtained.

Particularly preferred polycarboxylic acids employable for producing the polycarboxylic acid derivatives of the present invention are the following polycarboxylic acids:

(1) methyl vinyl ether-maleic acid copolymer (50:50, polymerization ratio), molecular weight: approx. 300,000–900,000;

(2) styrene-maleic acid copolymer (50:50), molecular weight: approx. 50,000–200,000; and (3) maleic acid-butyl acrylate copolymer (50:50), molecular weight: approx. 50,000–200,000.

The above-described polycarboxylic acids are well known and prepared, for instance, by the following method.

A monomer containing a carboxyl group such as acrylic acid, maleic acid or maleic anhydride and one or more of other comonomers such as methyl vinyl ether, styrene and acrylic acid ester are introduced into a solvent such as water, methanol, ethanol, ethyl acetate, toluene, acetone or methyl ethyl ketone and nitrogen gas is introduced into the resulting solution. To the solution is then added a polymerization catalyst such as benzoyl peroxide or azobis(isobutylonitrile), and the mixture is heated under stirring to obtain a polycarboxylic acid.

Certain polycarboxylic acids are commercially available. Examples of the commercially available polycarboxylic acids include a variety of methyl vinyl ether-maleic anhydride copolymers available from GAF, U.S.A. under the tradename of GANTREZ.

Details of processes for the preparation of polycarboxylic acids is described, for instance, in "Experimental Procedures for Vinyl Polymerization" (by Takayuki Otsu & Ki-ich Takemoto, published by Kyoritsu Publishing Co., Japan, 1964).

There is no specific limitation on the nonionic surface active agent to be attached to the polycarboxylic acid, as far as the nonionic surface active agent contains a hydroxyl group in the molecule. Preferred is a nonionic surface active agent having a repeating unit of the formula (II):

$$-CH_2CH_2O- \quad (II)$$

The above-described nonionic surface active agent particularly preferably has the formula (III):

$$R-CH_2CH_2O_nH \quad (III)$$

in which R is an alkyl group having 2–22 carbon atoms, an aryl group having an alkyl group of 4–12 carbon atoms as a substituent, an alkylcarbonyloxy group having an alkyl group of 9–19 carbon atoms, a sorbitane (1,4-anhydroglucitol or 1,5-anhydroglucitol) or sorbitol (glucitol) residue having at least one hydroxyl group esterified with a carboxylic acid having 2–22 carbon atoms; and n is an integer of 2–40.

Examples of the above-described nonionic surface active agent having the formula (III) include following compounds:

(1) polyoxyethylene alkyl ether (a compound having the formula (III) in which R is an alkyl group having 2–22 carbon atoms), for instance, a compound having an alkyl group such as ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, isopropyl, isobutyl or isoamyl, and 2–40 oxyethylene groups in a molecule;

(2) polyoxyethylene alkylphenyl ether (a compound having the formula (III) in which R is a phenyl group having an alkyl group of 4–12 carbon atoms as a substituent), for instance, a compound having an alkyl group such as pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, isobutyl or isoamyl, and 3–40 oxyethylene groups in a molecule;

(3) polyoxyethylene alkyl ester (a compound having the formula (III) in which R is an alkylcarbonyloxy group having an alkyl group of 9–19 carbon atoms), for instance, a compound having an alkyl group such as nonyl, decyl, undecyl, dodecyl, tridecyl, tetradecyl, pentadecyl, hexadecyl, heptadecyl, octadecyl, nonadecyl or eicosyl, and 2–40 oxyethylene groups in a molecule;

(4) aliphatic carboxylic acid ester of polyoxyethylene sorbitane (a compound having the formula (III) in which R is a sorbitane residue having at least one hydroxyl group esterified with an aliphatic carboxylic acid of 2–22 carbon atoms, for instance, a compound having a sorbitane residue esterified with one to three aliphatic carboxylic acids such as acetic acid, propionic acid, butyric acid, valeric acid, caproic acid, enanthic acid, caprylic acid, capric acid, undecylic acid, lauric acid, myristic acid, palmitic acid, stearic acid, oleic acid, arachic acid, behenic acid, isopropionic acid, isobutyric acid, isovaleric acid or isostearic acid, and 2–40 oxyethylene groups in a molecule;

(5) aliphatic carboxylic acid ester of polyoxyethylene sorbitol (a compound having the formula (III) in which R is a sorbitol residue having at least one hydroxyl group esterified with an aliphatic carboxylic acid of 2–22 carbon atoms), for instance, a compound having a sorbitol residue esterified with one to four aliphatic carboxylic acids such as acetic acid, propionic acid, butyric acid, valeric acid, caproic acid, enantic acid, caprylic acid, capric acid, undecylic acid, lauric acid, myristic acid, palmitic acid, stearic acid, oleic acid, arachic acid, behenic acid, isopropionic acid, isobutyric acid, isovaleric acid or isostearic acid, and 2–40 oxyethylene groups in a molecule; and (6) same compounds as the above-described compounds (1) through (5) except that oxypropylene groups in the form of a block or random copolymer is contained in addition to the oxyethylene groups.

The constituent and embodiments of the analytical element of the present invention will be illustrated hereinafter more in detail, by referring to a multilayer analytical element comprising a color reaction layer and a coupler substrate layer provided thereon in which said reaction layer comprises a diazonium compound useful for quantitative analysis of hydrolase such as amylase and a binder.

The diazonium compound contained in the color reaction layer is a compound forming color upon a diazo reaction, and representative examples thereof are as follows:

(A)

(B)

-continued

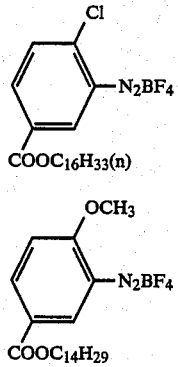

(C)

(D)

These diazonium compounds are those being able to produce diazo dyes well known in the arts of photography, and are also known as color-forming compounds in analytical chemistry. The synthesis method is described in detail, for instance, in "Dye Chemistry" by Yutaka Hosoda (Gihodo, Japan, 1968, pp. 137–149).

The color reaction layer can be formed by procedures of applying a solution containing the aforementioned polycarboxylic acid derivative binder and diazonium compound (generally, an aqueous solution containing an organic solvent) to prepare a layer, and then drying the solution layer by an appropriate method. The amount of the diazonium compound is determined according to the reaction equation of the color reaction in which an analyte for analysis participates. The color reaction layer is formed in such manner that the resulting dried layer has a thickness of approx. 1–50 μm and preferably approx. 2–30 μm.

The coupler substrate layer provided on the color reaction layer is a layer containing a coupler substrate, i.e., a non-diffusive coupler consisting essentially of a substantially colorless substrate which has a color-forming group capable of forming a dye upon reaction with a diazonium compound and produces a diffusive product under action of an analyte in the presence of water. The coupler substrate layer can be formed, for instance, by procedures of applying an aqueous solution or dispersion containing the above-described non-diffusive coupler and a hydrophilic binder onto the surface of the color reaction layer and then drying the so applied layer by an appropriate method.

Since a low molecular weight product carrying the color-forming group produced upon enzymic decompostion of the substrate needs to diffuse in the hydrophilic binder for participating in the color formation reaction, the color forming group preferably has a solubilizing group such as a sulfonic group, carboxyl group or hydroxyl group. The solubilizing group can be introduced between the under-mentioned linking group.

Examples of the color-forming group attached to the non-diffusive substrate through a linking group include a variety of couplers generally proposed for the photographic process such as pyrazolin-5-one, naphthol, phenol and acylacetonitrile. Since these couplers need to be attached through a linking, they are required to have a group such as an amino group or a hydroxyl group. Also employable is a two equivalent coupler having a releasing group at the coupling position, which is well known in the art of photography.

In addition to the above-described couplers, arylamines such as N,N-dimethylphenylenediamaine, N-methyl-N-(2,3-epoxy)propylaniline and N-methyl-N-hydroxymethylaniline.

The color forming group is chosen according to a number of factors such as influence to the aimed enzymic reaction, easiness in the synthesis, and stability of the compound at the optimum pH for the enzymic reaction. The color-forming group should diffuse into the color reaction layer together with a diffusive compound originating from a substrate which is produced by degradation of the substrate through an enzymic reaction. Accordingly, the color-forming group itself preferably is diffusive.

For obtaining the coupler substrate in which an appropriately selected color-forming group is attached to a non-diffusive substrate through a linking group, an art for "Reactive Dyes" being broadly employed in a field of dyestuffs can be utilized. For instance, "The Chemistry of Synthetic Dyes" Vol. VII, by K. Venkataraman (Academic Press, New York, 1972) shows detailed examples of the linking groups which provides a linkage between dye molecules and molecules of natural polymers such as various celluloses and proteinous fibers such as wool and silk, and methods for the preparation of linkage. In the preparation of non-diffusive substrate employable in the present invention, these techniques can be employed to provide a linkage between a color-forming group and a non-diffusive substrate, so as to obtain a compound serving as the coupler substrate.

Preferred examples of the linking group include s-triazine residues such as s-triazine-2,4-diyl, s-triazine-2,4,6-triyl and 6-chloro-s-triazine-2,4-diyl, pyrimidine residues such as pyrimidine-2,4-diyl, pyrimidine-2,5-diyl, pyrimidine-2,4,6-triyl and 4,5-dichloropyrimidine-2,6-diyl, and oxy groups.

Examples of the color-forming group include the following groups, in which 5-pyrazolone means 2-pyrazolin-5-on;

4,6-bis(8-hydroxy-3,6-disulfo-1-naphthylamino)-s-triazin-2-yl;
4-anilino-6-(8-hydroxy-3,6-disulfo-1-naphthylamino)-s-triazin-2-yl;
4-chloro-6-(8-hydroxy-3,6-disulfo-1-naphthylamino)-s-triazin-2-yl;
4-chloro-6-(1-p-sulfophenyl-5-pyrazolon-3-ylamino)-s-triazin-2-yl;
4,5-dichloro-6-(8-hydroxy-3-sulfo-1-naphthylamino)-2-pyrymidyl;
4-chloro-6-[3-(1-m-sulfophenyl-5-pyrazolon-3-ylamino)anilino]-s-triazin-2-yl;
4-m-sulfoanilino-6-(2-hydroxy-5-chloroanilino)-s-triazin-2-yl;
4-(8-hydroxy-3,6-disulfo-1-naphthylamino)-6-(1-phenyl-5-pyrazolon-3-ylaminio)-s-triazin-2-yl;
4-[β-(N-ethyl-4-trichloromethylanilino)ethoxy]-6-(8-hydroxy-3,6-disulfo-1-naphthylamino)-s-triazin-2-yl;
4-p-sulfoanilino-6-(3-p-sulfophenyl-4,4-dichloro-5-pyrazolon-3-ylamino)-s-triazin-2-yl;
a group containing sulfonato group ($-SO_3^-$) and an alkali metal cation (e.g., $Li^+$, $Na^+$ and $K^+$) as a counter ion thereof instead of the sulfo group in the above-described groups; and
a group in which the (13,3-trimethyl-6-p-formylphenyl-6-azoniaoctyl)oxy group is combined with chlorine anion as a counter ion.

If the coupler substrate having the above-described color-forming group diffuses from the original position in a coupler substrate layer into a color reaction layer under no action of analyte, fogging, namely color formation independent of the analyte action, takes place. Since the production of fog lowers the accuracy of the analysis, the fogging should be sufficiently avoided.

In preparing a coupler substrate layer through a coating procedure, a coupler substrate is dissolved or dispersed in a binder solution containing one or more polymers, and the so prepared solution or dispersion is coated and dried to form a layer. However, if the coupler substrate has a high molecular weight, the coupler substrate layer can be formed without using a binder through a procedure such as a coating procedure or impregnation procedure. For instance, a material such as a paper sheet, a cloth sheet or a hard plastic film is initially impregnated with the coupler substrate, and thus impregnated material is superposed on a color reaction layer through a procedure such as laminating to form a coupler substrate layer.

A variety of hydrophilic binders are employable for the preparation of the coupler substrate layer. Examples of the hydrophilic binder include hydrophilic natural polymers such as gelatin, agarose, sodium alginate and carboxymethyl cellulose, and hydrophilic synthetic polymers such as polyacrylamide, poly(vinyl alcohol), poly(vinylpyrrolidone), poly(sodium acrylate), poly(hydroxyethyl methacrylate), acrylic acid copolymers and maleic acid copolymers.

An appropriate binder is selected from these binders in consideration of employed conditions, characteristics of analyte, coating properties, and the like. For instance, gelatin is not appropriate as a binder for the use in an analytical element for the analysis of protease, and generally employed for that purpose is agarose. If an analyte has high molecular weight (e.g. amylase), a binder having a high expansion coefficient such as polyacrylamide is desirably employed to make an analyte efficiently diffusive into a coupler substrate layer. The congeniality between an analyte and a binder based on the molecular weight is generally known in the pertinent art, and no further description is required.

Generally appropriate hydrophilic binder polymers are polymers such as agarose, polyacrylamide, poly(sodium acrylate) and acrylic acid copolymers.

In addition to the non-diffusive coupler substrate and hydrophilic binder, a variety of additives, for instance, a surface active agent, a pH adjusting reagent, a fine powder, an antioxidant and other organic or inorganic additives, can be incorporated into the coupler substrate layer for improvement of various characteristics with respect to the coating procedure, and diffusion, reaction and preservation of the diffusive compound.

There is no specific limitation on thickness of the coupler substrate layer, but the layer preferably has a thickness of approx. 1–50 $\mu$m, preferably a thickness of approx. 2–30 $\mu$m, if the layer is provided by the coating procedure. However, if the layer is formed by other processes such as a laminating process, the thickness of the coupler substrate layer can widely vary in the range of from several dozens $\mu$m to several hundreds $\mu$m.

The multilayer analytical element basically comprises the above-mentioned coupler substrate layer and color reaction layer, but if necessary, a light-transmissive, water-impermeable support can be provided on the lower surface of the color reaction layer (side not facing the coupler substrate layer). Examples of the support include various known films such as a poly(ethylene terephthalate) film, a cellulose ester film (e.g. films of cellulose diacetate, cellulose triacetate and cellulose acetate propionate), a polycarbonate film and poly(methyl methacrylate) film, and a glass plate. These water-impermeable transparent support is employed with a thickness of from approx. 50 $\mu$m to approx. 2 mm.

If the adhesion between the support and the color reaction layer is not enough in the case of a hydrophobic support is employed, the support needs to be subjected to a variety of known pretreatments, such as, treatments for imparting hydrophilic property to the surface of the support (e.g., irradiation of ultraviolet rays, irradiation of electron beams, flame treatment, and hydrolyzing treatment by an alkali agent). Otherwise, a subbing layer having an adhesive material appropriate for both the support and the hydrophilic binder of the reagent layer is provided on the surface of support, or finely depressed and protruded portions are provided onto the surface of support under the conditions that the light-transmissivity is not noticeably reduced.

The multilayer analytical element can further comprise other various functional layers for the purpose of preventing diffusion, uniformly spreading the introduced sample, light-blocking and enhancement of adhesion, as need arises.

A diffusion-preventive layer can be provided to serve as a layer to completely prevent diffusion of a non-diffusive substrate having been not subjected to the analyte action into other layers and at the same time not to prevent diffusion of a reaction product provided with diffusive propety by the action of analyte. The diffusion-preventive layer also serves for preventing diffusion of a diazonium compound contained in the color reaction layer into the coupler substrate layer. Materials employable for preparation of th diffusion-preventive layer are the same hydrophilic polymers as those employable for the preparation of the aforementioned coupler substrate layer. Among these polymers, particularly suitable are gelatin, agarose and poly(vinyl alcohol), and these polymers have properties appropriate for differentiating the diffusion property of the non-diffusive substrate from that of the reaction product (diffusive compound). Into the diffusion-preventive layer, various additives same as those described for the aforementioned coupler substrate layer can be incorporated, if necessary.

The diffusion-preventive layer is, as is understandable from its function, arranged between the coupler substrate layer and the color reaction layer, and generally has a thickness of approx. 0.5–5 $\mu$m.

The multilayer analytical element can comprise a spreading layer on the coupler substrate layer (side adverse to side facing the color reaction layer). The spreading layer is a layer made of fibrous or non-fibrous porous medium and serves for almost uniformly spreading a liquid sample containing analyte upon application onto the layer, and introducing the liquid sample into the coupler substrate layer.

Examples of the porous medium include non-fibrous medium such as polymer membranes for filtration purpose of various pore sizes (membrane filter), Sephadex, agarose and dextran. Further, a variety of fibrous materials such as natural fibers (e.g., pulp, cotton, silk and wool), semi-synthetic fibers (e.g., cellulose ester and viscose rayon), synthetic fibers (e.g., polyamide, polyester and polyolefin), and fibrous inorganic materials (e.g., glass fiber, colored glass fiber and asbestos) can be employed in the form of fabrics, felt, non-woven fabrics having continuous voids, or the like.

A blushed polymer (generally called "membrane filter") can be also employed as the spreading layer. Further employable are a blushed polymer having a structure wherein a porous substance such as diatomaceous earth or microcrystal substance (e.g., microcrystal cellulose) is uniformly dispersed in a binder, a blushed polymer having a structure wherein finely spherical beads such as glassbeads or synthetic polymer beads are kept in point-contact therebetween in a binder, and a blushed polymer having a uniformly dispersed fine powder such as $TiO_2$ or $BaSO_4$. As examples of hydrophilicly treated fabrics, there are mentioned a fabric subjected to procedures of washing with water for defatting, and drying a fabric subjected to procedures of washing with water for defatting, drying and then incorporating thereinto a small amount of a surface active agent, a wetting agent, a hydrophilic polymer, or a hydrophilic polymer containing a dispersed fine powder such as $TiO_2$ or $BaSO_4$. Those fabrics and the techniques for using the fabrics as the spreading layers are described in detail in U.S. Pat. No. 4,292,272, and the fabrics can be employed for the multilayer analytical element according to the description.

The spreading layer generally has a thickness of from approx. 50 μm to 1 mm, preferably from approx. 80 μm to 400 μm, and more preferably from approx. 100 μm to 300 μm.

Between the coupler substrate layer and the color-reaction layer of multilayer analytical element can be arranged a color-blocking layer or a light-reflecting layer. Further, an adhesive layer capable of permeating a liquid sample therethrough can be arranged between the spreading layer and the color-blocking layer or light-reflecting layer to increase the adhesion of the spreading layer. The color-blocking layer, light-reflecting layer and adhesive layer are described in detail in the publications mentioned before, and those layers can be provided within the multilayer analytical element according to the descriptions.

Examples of the color-blocking layer or light-reflecting layer include a layer of a white powder such as $TiO_2$ powder or $BaSO_4$ powder dispersed in a hydrophilic polymer binder, with a thickness of approx. 1–50 μm, preferably approx. 2–20 μm; a layer of a powder with white or pale metallic luster such as aluminum powder dispersed in a hydrophilic polymer binder, with a thickness of approx. 2–50 μm, preferably approx. 2–20 μm; or a liquid sample-permeable porous metal layer made of a white or pale metal such as aluminum, with a thickness of approx. 5–100 μm, preferably approx. 5–50 μm.

The adhesive layer can be prepared from the same kind of polymers as that employable as the binder of the coupler substrate layer, color-blocking layer or light-reflecting layer, which allow permeation of the liquid sample and analyte both, with a thickness of approx. 0.5–10 μm, and preferably approx. 0.7–5 μm. The spreading layer can be provided on the adhesive layer of a hydrophilic polymer by the following procedures. A hydrophilic polymer solution is initially applied onto a coupler substrate layer, a color-blocking layer or a light-reflecting layer. After the so coated solution is half-dried or dried, a surface of the adhesive layer is wetted with water or an aqueous surface active agent solution. On the so wetted surface of the adhesive layer is placed a porous material sheet, and then appropriate pressure is applied thereonto to uniformly fix the spreading layer (porous material sheet) onto the adhesive layer. A multilayer analytical element having a well fixed spreading layer can be also obtained by coating a solution or dispersion capable of forming a porous layer over the adhesive layer.

The present invention will be further described hereinafter by referring to a multilayer analytical element for analysis of amylase activity.

A multilayer analytical element for the amylase analysis, which is one embodiment of analytical elements according to the present invention, has a constituent comprising a coupler substrate layer, a diffusion-preventive layer, and a color reaction layer superposed in this order on a transparent plastic film, in which the coupler substrate layer comprises a compound having an amylose bonding serving as a substrate of amylase (e.g., non-diffusive substrate wherein starch carries color-forming groups) and a hydrophilic binder; and the color reaction layer comprises a diazonium compound reactive to the color-forming groups attached to the substrate to generate a color and a hydrophilic binder.

The starch molecule is non-diffusive because it is as such of very large size. Therefore, the starch molecule is not diffused into the color reaction layer prior to the reaction, and thus the color-forming groups and the diazonium compound are kept separately. For this reason, the multilayer analytical element is substantially colorless.

When an aqueous solution containing amylase (analyte) is spotted onto the substrate layer, amylase diffuses to enter the substrate layer together with the aqueous medium. Then hydrolysis proceeds under action of amylase, so as to degrade the starch carrying the coupler molecules. Oligosaccharides carrying the color-forming groups (diffusive compound) produced by the enzymic degradation diffuses into the color reaction layer, where a coupling reaction proceeds between the oligosaccharide and the diazonium compound to produce a dye. The amylase activity is in proportion to the hydrolysis rate of starch. On the other hand, the color forming rate is in proportion to the amount of oligosaccharide carrying the color-formation groups introduced into the color reaction layer. Accordingly, the amount of a dye produced within a certain period of time is measured by colorimetry to determine the amylase activity.

The rate of the color formation reaction measured as described above is applied to a calibration curve prepared using an amylase solution containing a previously known amount of amylase, whereby the desired amylase activity of the analyte is determined. In this method, since the multilayer analytical element is substantially colorless before the analyte solution is spotted thereon, an optical density value obtained upon the reaction by colorimetry is in proportion to the amount of a dye formed as a result of the enzymic reaction. Accordingly, the separation of the substrate reaction product from the unreacted substrate prior to the colorimetry is unnecessary, while this separation is required in the conventional method employing a dye-containing starch (dye-containing substrate) such as blue starch, that is, the blue starch method or a dry analysis method described in Japanese Patent Provisional Publication No. 53(1978)-131089.

The multilayer analytical element according to the invention can be subjected to a colorimetry utilizing a transmitting light if the light-blocking layer is not arranged.

The multilayer analytical element will be further described hereinafter with respect to the constituent and materials.

Typical layer arrangements of the multilayer analytical elements according to the present invention are illustrated in the accompanying drawings. FIG. 1 shows a multilayer analytical element composed of a light-transmissive, water-inpermeable support 10, on which are provided in order from far side of the support 10, a coupler substrate layer 50 and a color reaction layer 20.

The coupler substrate layer 50 comprises a substantially colorless non-diffusive substrate enclosed within a hydrophilic binder, in which the non-diffusive substrate carries the color-forming groups capable of forming a dye through a reaction with a diazonium compound and gives under action of the analyte substantially colorless diffusive products carrying the color-forming groups and being diffusive in the hydrophilic binder in the presence of water. The color reaction layer 20 comprises in the polycarboxylic acid derivative binder a diazonium compound capable of forming dye through a reaction with the above-mentioned color-forming groups. Accordingly, the non-diffusive substrate is included separately from the diazonium compound in the multilayer analytical element.

Figure 2:
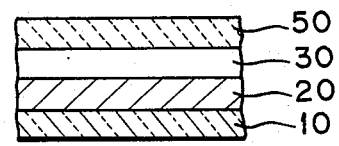
FIG. 2 illustrates a multilayer analytical element composed of a support, a color reaction layer, a diffusion-preventive layer and a coupler substrate layer.

FIG. 2 shows a multilayer analytical element comprising a diffusion-preventive layer 30 arranged between the color reaction layer 20 and the coupler substrate layer 50. The function of the diffusion-preventive layer will be illustrated in detail hereinafter.

Figure 3:
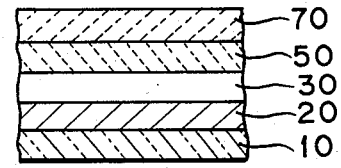
FIG. 3 illustrates a multilayer analytical element composed of a support, a color reaction layer, a diffusion-preventive layer, a coupler substrate layer and a spreading layer.

FIG. 3 is a conceptional view showing a multilayer analytical element having a different layer constitution, which comprises a light-transmissive, water-inpermeable support 10, on which are provided in order the color reaction layer 20, the diffusion-preventive layer 30, the coupler substrate layer 50, and a spreading layer 70.

In the case of using the multilayer analytical element of FIG. 3, when a liquid sample containing analyte (e.g., amylase) is spotted onto the spreading layer 70, the liquid sample speads almost uniformly in the spreading layer 70 and permeates into the coupler substrate layer 50. In the coupler substrate layer 50, a diffusive compound is produced from the non-diffusive substrate by action of the analyte. The diffusive compound diffuses from the coupler substrate layer 50 into the color reaction layer 20 passing through the diffusion-preventive layer 30. Since the diffusive compound (reaction product) carries color-forming groups, the color-forming groups react with the diazonium compound to form a dye when the diffusive compound reaches the color reaction layer 20. If the analyte is hydrolase, the hydrolase having high molecular weight is unable to pass through the diffusion-preventive layer 30, and stays as well as the non-diffusive substrate in the coupler substrate layer 50. As a result, a dye produced is in proportion to the hydrolase activity. Accordingly, the hydrolase activity of the liquid sample spotted to the analytical element can be determined by measuring the amount of so produced dye. For the measurement of the amount of dye, colorimetric measurement based on light transmission or light reflection of the dye within the absorption wavelength region thereof is appropriately employed, but an eye measurement can be also employed depending upon the purpose or required accuracy.

Figure 4:
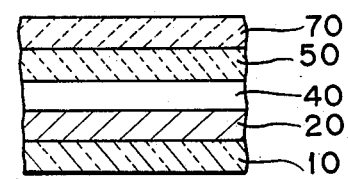
FIG. 4 illustrates a multilayer analytical element composed of a support, a color reaction layer, a light-blocking layer, a coupler substrate layer and a spreading layer.

FIG. 4 shows a multilayer analytical element comprising a light-blocking layer 40 provided instead of the diffusion-preventive layer 30 in the multilayer analytical element shown in FIG. 3.

The analytical element of the present invention will be hereinafter described more in detail, by referring to the simple multilayer analytical element of FIG. 1. Description on other additional layers illustrated in the multilayer analytical elements shown in FIGS. 2 through 4 will be added to the above description, in order to make this illustration more understandable.

The coupler substrate layer 50 is colorless because the non-diffusive substrate is substantially colorless. The color reaction layer can be also made colorless by employing a colorless diazonium compound. Since each of layers has a thickness of not higher than approx. 50 $\mu$m, those layers are transparent, and thus the multilayer analytical element shown in FIG. 1 is transparent.

Upon application of a liquid sample containing analyte (aqueous solution, namely, a solution or a dispersion containing water as a solvent or a dispersing medium) to the multilayer analytical element, the non-diffusive coupler substrate is subjected to a chemical reaction such as hydrolysis reaction under action of the analyte within the coupler substrate layer, giving a colorless diffusive product. The colorless diffusive product diffuses into both a hydrophilic binder matrix of the coupler substrate layer 50 and the polycarboxylic acid derivative binder matrix of the color reaction layer 20 in the presence of water supplied with the analyte. The diffusive product then undergoes a diazo coupling reaction upon contact with the diazonium compound contained in the color reaction layer 20, producing a dye. After the reaction proceeds for a fixed period of time under predetermined conditions, the amount of dye produced in the color reaction layer 20 is measured by colorimetry, whereby the amount of analyte of activity value of analyte contained in the liquid sample is determined.

The multilayer analytical element is, as described hereinbefore, effective for the measurement of hydrolase activity contained in an aqueous liquid sample, especially a body fluid such as blood, urine, saliva, spinal fluid, intestinal juice and pancreatic juice. In any one of the conventional methods for measuring the activity of hydrolase contained in blood such as amylase, blood plasma or serum ought to be separated from a whole blood by a procedure such as centrifugal separation, and the so separated blood plasma or serum is employed as a liquid sample. The above separation method is needed, because the hemoglobin contained in a large amount in the whole blood interferes with the colorimetry.

By providing a light-blocking layer as one of functional layers in the multilayer analytical element, the measurement of enzymic activity can be carried out employing a whole blood as a liquid sample, which is impossible in the conventional methods.

The above-described multilayer analytical element is an analytical element in which a color formation reaction proceeds only when a liquid sample is applied to the element. Accordingly, a colorimetric procedure after the color formation reaction can be carried out from the bottom surface of the element, and transmission colorimetry and reflection colorimetry can be employed.

If a light-blocking layer having a high light-scattering property is provided between the color reaction layer and the coupler substrate layer in the multilayer analytical element, the interference caused by erythrocyte or hemoglobin reaching the surface of the coupler substrate layer can be blocked. For this reason, the enzymic activity can be determined using a whole blood through reflection colorimetry which involves measurement of a color density of the color reaction layer through the transparent support.

One example of the multilayer analytical element having the above-described layer constituent is shown in FIG. 4. Since the light-blocking layer 40 as such has a function of preventing diffusion of a diffusive, interfering substance and/or diazonium compound, provision of the diffusion-preventive layer is not necessary. Moreover, although interfering substances such as hemoglobin, bilirubin and chyle may migrate into a serum, the above-mentioned layer having the diffusion-preventive function can completely block the diffusion of the interfering substances into the lower layer. Accordingly, the multilayer analytical element having the light-blocking layer makes possible the analysis of a serum sample containing substances such as hemoglobin, high bilirubin or chyle, with high accuracy.

The non-diffusive substrate employable for the multilayer analytical element having the above-mentioned constituent is a substance whose physical properties such as molecule size, forms and dissociation degree noticeably vary under action of analyte, resulting in noticeable increase of diffusive property within the hydrophilic binder layer. Examples of the non-diffusive substrate include a variety of substrates of enzyme contained in body fluids. Among these substrates, hydrolase can be effectively applied to the multilayer analytical element, and examples of the hydrolase include protease such as trypsin, chymotrypsin and pepsine, amylase, lipase, and pectinase. In the case that the above-mentioned hydrolase is employed as analyte, a substrate of hydrolase, that is, protein, amylose, glyceride or pectin, respectively, is employed in combination with substantially colorless color-forming group.

In the above, a multilayer analytical element composed of a color reaction layer comprising a diazonium compound and the polycarboxylic acid derivative and a coupler substrate layer is described in detail as one representative embodiment of the multilayer analytical elements according to the present invention, but the analytical element of the invention is by no means restricted to the above-described analytical element.

Figure 5:
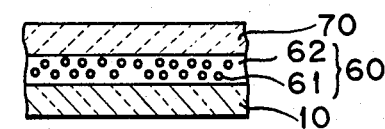
FIG. 5 illustrates a multilayer analytical element composed of a support, a reagent layer (comprising a color reactive phase and a coupler substrate phase placed in a single layer form) and a spreading layer.

For instance, in the multilayer analytical element, the color reaction layer and coupler substrate layer are not necessarily provided in the form of the laminated layers. As illustrated in FIG. 5, a reagent layer can be composed of a single layer in which a capsular color reaction phase 61 comprising a diazonium compound and the polycarboxylic acid derivative is present separately from a coupler substrate phase 62.

In FIG. 5, the provision of the spreading layer 70 can be omitted if a liquid sample is introduced uniformly or almost uniformly by means of a separate apparatus, device or the like. Furthermore, if the reagent layer is self-supporting, a light-transmissive, water impermeable support is not essential for the analytical element. In other words, the analytical element of the present invention can be composed of a single reagent layer depending upon the purpose and the required analytical accuracy.

As for the substance to be analyzed (analyte) for the analytical element of the present invention, various substances can be analyzed as described hereinbefore. Further, as for the physical constituent and reagents of the analytical element, a variety of physical and chemical constituents can be adopted in the present invention according to the analytical purpose and analytical accuracy.

As described before, substances contained in a body fluid such as cholesterol, triglyceride (neutral fat), glucose and uric acid, which are decomposable under action of oxydoreductase, particularly oxidase corresponding to each substance, to generate hydrogen peroxide and a low molecular weight product, can be analyte for the analytical element of the present invention. The decomposing enzyme (oxidase) generally has an optimum pH range for the enzymic action on an acidic side, and therefore the reagent layer of an analytical element can be advantageously prepared by employing the polycarboxylic acid derivative binder of the present invention.

Alternatively, a quantitative analysis can be accomplished on the basis of the fact that the above-described substances contained in a body fluid reacts with oxidase to produce hydrogen peroxide, by the following manner: a color-forming composition capable of undergoing a color-forming coupling reaction in the presence of the hydrogen peroxide and peroxidase, for instance, a combination of 1,7-dihydroxynaphthalene, 4-aminoantipyrine and peroxidase is previously contained in the reagent layer or other layers such as a layer adjacent to the reagent layer, and then almost the same procedure of the aforementioned amylase analysis employing the coupler substrate and a diazonium compound is done, whereby to obtain the quantitative analysis.

The present invention is further illustrated by the following examples, but these examples are by no means intended to restrict the present invention. A coupler starch employed in Examples 1 through 3 and comparison Examples 1 through 3 was obtained through the following synthesis procedure.

SYNTHESIS PROCEDURE (1) Synthesis of Color-Forming Group (Reactive Coupler)

A reactive coupler, 2-[8-hydroxy-3,6-bis(sodium sulfonato)-1-naphthylamino]-4,6-dichloro-s-triazine, is prepared from cyanuric chloride and 1-amino-8-hydroxynaphthalene-3,6-disulfonic acid (H acid) monosodium salt (referred to hereinafter as "H acid-Na salt") according to a method by J. T. Thurstton et al., J. Amer. Chem. Soc., 73 (7), 2981-29 (1951).

36.9 g. of cyanuric chloride was dissolved in 150 ml. of hot acetone. The resulting solution was poured into 500 ml. of ice water to prepare a suspension. Into the suspension kept at 0°-4° C. was then dropped 300 ml. of an aqueous solution containing 140 g. of the H acid-Na salt and 16 g. of sodium peroxide. Subsequently, into the suspension was dropped 250 ml. of 2-N aqueous sodium hydroxide solution. The temperature of reaction liquid was gradually increased to room temperature, and the liquid was stirred for 1 hour. The reaction liquid was then poured into 4 l. of acetone to give a precipitate, and the precipitate was collected by filtration. Thus collected precipitate showed a ultra-violet absorption spectrum different from that of the H acid, and a high speed liquid chromatographic analysis indicated that the desired product (reactive coupler) was contained in the precipitate in an amount of not less than 90%.

(2) Synthesis of Non-Diffusive Substrate Carrying Color-Forming Groups (Coupler Starch)

20 g. of sodium hydroxide was dissolved in 2 l. of water. To the solution was added 46 g. of corn starch and the resulting mixture was stirred to prepare a clear paste. To the paste was added 12 g. of the reactive coupler obtained in the above-described procedure (1) and the mixture was stirred at room temperature for 8 hours. The reaction liquid was neutralized with diluted hydrochloric acid, and then to the liquid was added 1.5 l. of acetone to give a precipitate of starch. The supernatant liquid was removed by decantation, and the precipitate was then dissolved in 2 l. of distilled water. After the precipitate was dissolved, 5 g. of sodium chloride and 1.5 g. of acetone were successively added to the solution to give another precipitate. The procedure was repeated three times to remove an unreacted material and a low molecular weight compound from the precipitate.

Thus obtained precipitate was the desired coupler starch, and the precipitate was freeze-dried. The coupler starch was swollen with water and then finely particulated by a particulating device. Thus the coupler starch was easily dissolved in water. The coupler starch was also dissolved homogeneously in an aqueous solution of sodium hydroxide (1% by weight solution), and the absorption spectrum of the coupler starch was confirmed to be same as that of the aforementioned reactive coupler.

The same reaction operations as above were repeated varying the addition ratio of the reactive coupler. As a result, the ractive coupler was introduced into starch in different ratios, to obtain coupler starches having various ratios ranging from 1/18 to 1/50 (the number of the reactive coupler molecule/the number of glucose unit).

To verify the enzymic activity of thus obtained coupler starch, the color forming ability was colorimetrically checked by a method similar to that for commercially available reference dye-attached starch, Dyamyl-L (trade name) for quantitative analysis of amylase.

In 25 ml. of distilled water were dissolved 460 mg. of the coupler starch, 140 mg. of monopotassium phosphate and 176 mg. of dipotassium phosphate to prepare a solution of coupler starch. As a color forming liquid, 5 g. of distilled water containing 300 mg. of commercially available Fast Red B Salt: CI-37125 containing approx. 20% by weight of diazonium salt was employed.

As the reference amylase solution, a liquid sample prepared by diluting saliva with an aqueous solution containing 0.9% sodium chloride and 7% albumin, which was determined to be at 200 Somogyi unit/dl.

(3) Procedure

Each of two test tubes (A and B) was charged with 1 ml. of the coupler starch solution, and each of other test tubes (C and D) was charged with 1 ml. of the dye-attached substrate (Dyamyl-L) solution. The test tubes were incubated at 37° C. for 3 min. Then, into each of the test tubes A and C was introduced a 100 μl. of the reference amylase solution, and into each of the test tubes B and D was introduced at 100 μl. of an aqueous solution containing 0.9% sodium chloride and 7% albumin.

The test tubes were then incubated at 37° C. for 10 min, and to each of the liquid samples in the test tubes was added 4 ml. of Dyamyl-L precipitant to terminate the enzymic reaction of amylase.

Subsequently, to the liquid samples in the test tubes A and B were further added the above-described color-forming liquid of diazonium salt in the amount of 100 μl.

Each of the liquid samples in the test tubes was subjected to centrifugal separation at 300 r.p.m. for 10 min, and then the supernatant was colorimetrically measured by applying a light having a wavelength of 530 nm for the liquid samples of test tubes A and B, and a light having a wavelength of 540 nm for the liquid samples of test tubes C and D. Thus, the optical density was determined. The results are set forth in Table 1.

TABLE 1

|  | A | B | Difference of Optical Density |
|---|---|---|---|
| Coupler Starch | 0.530 | 0.076 | 0.454 |
|  | C | D | Difference of Optical Density |
| Dyamyl-L | 0.507 | 0.067 | 0.440 |

The same procedures as mentioned above were carried out on the coupler starches having different combination ratios between the reactive coupler and the glucose unit, to obtain the wide range optical density value ranging from 0.23 to 1.9 in the supernatant liquid corresponding to that of the test tube A.

According to the verification experiments described above, it has been concluded that amylase acts normally on the coupler starches obtained in the aforementioned procedure (2).

EXAMPLE 1

A. Preparation of Analytical Element for Measurement of Amylase Activity (1) Preparation of Coating Solution for Forming Color Reaction Layer To 100 ml. of water were added 5 g. of methyl vinyl ether-maleic anhydride copolymer (molar ratio; 1:1, GANTREZ AN 139, trade name, produced by GAF, inherent viscosity[$\eta$]=1.0-1.4) and 1 g. of polyoxyethylene nonylphenyl ether (containing 10 oxyethylene groups in a molecule on average). The mixture was heated to 80° C. for 30 min. to undergo esterification reaction. Thus a binder solution was prepared.

Independently, in a mixed medium consisting of 2 ml. of acetone and 4 ml. of ethyl alcohol was dissolved 0.150 g. of 2-methoxy-5-tetradecyloxycarbonylbenzenediazonium tetrafluoroborate to prepare a diazonium salt solution. The so prepared solution was added to the above-described reaction liquid (binder solution) under stirring. After the addition was complete, the resulting liquid (a coating solution for forming a color reaction layer) was kept under observation for 20 min. The liquid remained transparent.

(2) Formation of Color Reaction Layer

On a transparent polyethylene terephthalate (PET) film having a gelatin subbing layer (thickness: 180 μm) was coated the coating solution prepared in the above-described procedure (1), and then dried at 50° C. by air to form a color reaction layer of 10 μm thick. Thus prepared dry color reaction layer showed high transparency.

(3) Formation of Diffusion-Preventive Layer

A mixture of 50 ml. of water, 80 g. of titanium dioxide fine powder and 0.5 g. of p-nonylphenoxyglycerol (25% aqueous solution) was sufficiently pulverized in a ball mill-type pulverizer. To the so pulverized mixture was added 300 g. of 3% aqueous agarose solution. The mixture was coated on the color reaction layer and dried to form a diffusion-preventive layer. Thus obtained diffusion-preventive layer had thickness of 6 μm after drying.

(4) Formation of Coupler Substrate Layer

A slurry was prepared by mixing 10 g. of the coupler starch obtained by the aforementioned synthesis procedure (number of reactive coupler molecules/number of glucose units=1/30), 2.6 g. of dipotassium hydrogen phosphate, 2.1 g. of monopotassium dihydrogen phosphate, 105 g. of water, 80 g. of polyacrylamide (5% aqueous solution) and 2 g. of p-nonylphenoxyglycerol (25% aqueous solution). The slurry was filtrated over a nylon-mesh sheet filter to prepare a coating solution for forming a coupler substrate layer.

(5) Provision of Spreading Layer

A mix-spinned fabric of polyester and cotton (mixed rate: polyester/cotton=75/25) was impregnated with an aqueous solution consisting of 150 g. of polyacrylamide (mean polymerization degree: 18,000, 0.8% aqueous solution) and 1 g. of p-nonylphenoxyglycerol (25% aqueous solution) to prepare a hydrophilic fabric.

A surface of the coupler substrate layer prepared as above was wetted with p-nonylphenoxyglycerol (0.2% aqueous solution), and then the hydrophilic fabric was fixed onto the surface of the coupler substrate layer under pressure, and finally dried.

B. Measurment of Amylase Activity

Fresh human saliva was diluted with a 7% alubumin physiological salt solution to prepare an amylase standard liquid having activity value of 6,000 U/1. 10 μl. of the amylase standard liquid was spotted onto the analytical element (analytical film) as prepared above to carry out hydrolysis reaction at 37° C. The hydrolysis reaction was observed by measuring a reflective density of the color reaction layer of the analytical element using Maccbeth reflection densitometer. The results are set forth in Table 2.

COMPARISON EXAMPLE 1

A. Preparation of Analytical Element for Measurement of Amylase Activity (1) Preparation of Coating Solution for Forming Color Reaction Layer The procedure of Example 1 was repeated except that 5 g. of methyl vinyl ether-maleic anhydride copolymer (inherent viscosity $[\eta]$=1.0–1.4) was dissolved in 100 ml. of Water to prepare a binder solution. To the binder solution was added under stirring the same diazonium salt solution as in Example 1. After the addition was complete, the resulting liquid (a coating solution for forming a color reaction layer) was kept under observation for 20 min. In the liquid, crystals precipitated.

(2) Formation of Color Reaction Layer

On the same PET film as in Example 1 was coated the coating solution prepared in the above-mentioned precedure (1) with thickness of 10 μm, and dried at 50° C. by air to form a color reaction layer. After dried, it was observed that a great amount of crystals precipitated over the surface of the color reaction layer.

Subsequently, a diffusion-preventive layer, a coupler substrate layer and a spreading layer were formed on the color reaction layer in the same manner as described in Example 1 to prepare a multilayer analytical element.

B. Measurement of Amylase Activity

The analytical element (analytical film) as prepared above was evaluated on the amylase activity in the same manner as in Example 1. The hydrolysis reaction caused by the amylase standard liquid having been applied to the analytical element was observed by measuring the reflective optical density of the color reaction layer. The results are set forth in Table 2.

TABLE 2

| Reaction Time (min.) | Reflective Optical Density of Color Reaction Layer | |
|---|---|---|
| | Example 1 | Com. Example 1 |
| 1 | 0.03 | 0.03 |
| 2 | 0.09 | 0.09 |
| 3 | 0.18 | 0.18 |
| 4 | 0.23 | 0.19 |
| 5 | 0.31 | 0.20 |
| 10 | 0.74 | 0.20 |
| 15 | 1.00 | 0.20 |
| 20 | 1.20 | 0.20 |

EXAMPLE 2

A. Preparation of Analytical Element for Measurement of Amylase Activity (1) Preparation of Coating Solution for Forming Color Reaction Layer To 100 ml. of water were added 5 g. of methyl vinyl ether-maleic anhydride copolymer (molar ratio; 1:1, GANTREZE AN 119, trade name, produced by GAF, inherent viscosity$[\eta]$=0.1–0.5) and 1 g. of polyoxyethylene monostearate (containing 10 oxyethylene groups in a molecule on average). The mixture was heated to 80° C. for 30 min. to undergo esterification reaction. Thus a binder solution was prepared.

Independently, in a mixed medium consisting of 1 ml. of acetone and 4 ml. of ethyl alcohol was dissolved 0.150 g. of 2-methoxy-5-tetradecyloxycarbonylbenzenediazonium tetrafluoroborate to prepare a diazonium salt solution. The so prepared solution was added to the aforementioned reaction liquid (binder solution) under stirring. After the addition was complete, the liquid (a coating solution for forming a color reaction layer) was kept under observation for 20 min. The liquid remained transparent.

(2) Formation of Color Reaction Layer

On a transparent polyethylene terephthalate (PET) film having a gelatin subbing layer (thickness: 180 μm) was coated the coating solution prepared in the above-described procedure (1), and then dried at 50° C. by air to form a color reaction layer of 10 μm thick. The dry color reaction layer showed high transparency.

Subsequently, a diffusion-preventive layer, a coupler substrate layer and a spreading layer were formed on the color reaction layer in the same manner as in Example 1 to prepare a multilayer analytical element.

B. Measurement of Amylase Activity

The analytical element (analytical film) prepared as above was evaluated on the amylase activity in the same manner as in Example 1. The hydrolysis reaction caused by the amylase standard liquid having been applied to the analytical element was observed by measuring the reflective optical density of the color reaction layer. The results are set forth in Table 3.

COMPARISON EXAMPLE 2

A. Preparation of Analytical Element for Measurement of Amylase Activity (1) Preparation of Coating Solution for Forming Color Reaction Layer The procedure of Example 2 was repeated except that 5 g. of methyl vinyl ether-maleic anhydride copolymer (inherent viscosity $[\eta]=0.1-0.5$) was dissolved in 100 ml. of water to prepare a binder solution. To the binder solution was added under stirring the same diazonium salt solution as in Example 2. After the addition was complete, the resulting liquid (a coating solution for forming color reaction layer) was kept under observation for 20 min. In the liquid, crystals precipitated (2) Formation of Color Reaction Layer On the same PET film as in Example 1 was coated the coating solution prepared in the above-mentioned procedure (1) with a dried thickness of 10 μm, and dried at 50° by air to form a color reaction layer. After dried, it was observed that a great amount of crystals precipitated over on the surface of the color reaction layer.

Subsequently, a diffusion-preventive layer, a coupler substrate layer and a spreading layer were formed on the color reaction layer in the same manner as in Example 1 to prepare a multilayer analytical element.

B. Measurement of Amylase Activity

The analytical element (analytical film) prepared as above was evaluated on the amylase activity in the same manner as in Example 1. The hydrolysis reaction caused by the amylase standard liquid having been applied to the analytical element was observed by measuring the reflective optical density of the color reaction layer. The results are set forth in Table 3.

TABLE 3

| Reaction Time (min.) | Reflective Optical Density of Color Reaction Layer | |
|---|---|---|
| | Example 2 | Com. Example 2 |
| 1 | 0.03 | 0.03 |
| 2 | 0.09 | 0.09 |
| 3 | 0.18 | 0.18 |
| 4 | 0.23 | 0.19 |
| 5 | 0.31 | 0.20 |
| 10 | 0.74 | 0.20 |
| 15 | 1.00 | 0.20 |
| 20 | 1.20 | 0.20 |

EXAMPLE 3 AND COMPARISON EXAMPLE 3

A. Preparation of Analytical Element for Measurement of Amylase Activity (1) Preparation of Coating Solution for Forming Color Reaction Layer To 100 ml. of water were added 5 g. of methyl vinyl ether-maleic anhydride copolymer (inherent viscosity $[\eta]=1.0-1.4$) and 1 g. of a nonionic surface active agent set forth in Table 4, and the resulting mixture was heated to 80° C. for 30 min. to undergo esterification reaction. Thus a binder solution was prepared.

Independently, in a mixed medium consisting of 2 ml. of acetone and 4 ml. of ethyl alcohol was dissolved 0.180 g. of 2-methoxy-5-tetradecyloxycarbonylbenzenediazonium tetrafluoroborate to prepare a diazonium salt solution. The so prepared solution was added to the aforementioned reaction liquid (binder solution) under stirring. After the addition was complete, the resulting liquid (a coating solution solution for forming a color reaction layer) was kept under observation for 20 min. The results are set forth in Table 4.

(2) Formation of Color Reaction Layer

On a transparent polyethylene terephthalate (PET) film having a gelatin subbing layer (thickness: 180 μm) was coated the coating solution prepared in the above-described procedure (1), and then dried at 50° C. by air to form a color reaction layer of 10 μm thick. After dried, the condition of the color reaction layer was observed. The results are set forth in Table 4.

TABLE 4

| Nonionic Surface Active Agent | | Coating Solution | Color Reaction Layer |
|---|---|---|---|
| Polyoxyethylene nonylphenyl ether | n = 2 | A | A |
| | n = 10 | A | A |
| | n = 18 | A | B |
| Polyoxyethylene octylphenyl ether | n = 3 | A | A |
| | n = 10 | A | A |
| | n = 30 | A | B |
| Polyoxyethylene lauryl ether | n = 2 | A | A |
| | n = 9 | A | A |
| | n = 21 | A | A |
| Polyoxyethylene stearyl ether | n = 4 | A | A |
| | n = 10 | A | A |
| | n = 25 | A | A |
| Polyoxyethylene monolaurate | n = 10 | A | A |
| Polyoxyethylene monostearate | n = 25 | A | A |
| Polyoxyethylene sorbitane monolaurate | n = 20 | A | A |
| Polyoxyethylene sorbitol tetraoleate | n = 30 | A | A |
| Comparison Example 3 | | B | B |

Remark: n represents the number of the oxyethylene group contained in the nonionic surface active agent molecule. Comparison Example 3 is, as well as Comparison Examples 1 and 2, an example employing methyl vinyl ether-maleic anhydride copolymer not carrying a nonionic surface active agent. Marks A and B in the above table means, A: transparent, and B: noticeable separation of crystals in the color reaction layer observed.

EXAMPLE 4

A. Preparation Analytical Element for Measurement of Cholesterol (1) Preparation of Coating Solution for Forming Color Reaction Layer To 100 ml. of water were added 5 g. of methyl vinyl ether-maleic anhydride copolymer (inherent viscosity$[\eta]=0.1-0.5$) and 2 g. of polyoxyethylene monostearate (containing approx. 25 oxyethylene groups in a molecule). The mixture was heated to 80° C. for 30 min. to undergo esterification reaction. Thus a binder solution was prepared.

Independently, in 2 ml. of acetone was dissolved 0.80 g. of 1,7-dihydroxynaphthalene to prepare a solution. The solution was then added to the aforementioned binder solution (reaction liquid). Then to the binder solution were successively added 0.9 g. of 4-aminoantipyrine and 40,000 IU of peroxidase (EC 1.11.1.7.) to prepare a coating solution for forming a color reaction layer.

(2) Formation of Color Reaction Layer

On a transparent polyethylene terephthalate (PET) film having a gelatin subbing layer (thickness: 180 μm) was coated the coating solution prepared in the above-described procedure (1), and then dried at 50° C. by air to form a color reaction layer of 10 μm thick. The dry color reaction layer remained highly transparent.

(3) Formation of Diffusion-Preventive Layer

In 50 ml. of water were dispersed 80 g. of titanium dioxide fine powder, 0.5 g. of polyoxyethylene p-isooctylphenyl ether (nonionic surface active agent), 8 g. of agarose, 100,000 IU of cholesterol esterase (EC 3.1.1.13) and 20,000 IU of cholesterol oxidase (EC.1.1.3.6). The dispersion was coated on the color reaction layer. Thus obtained dry diffusion-preventive layer had thickness of 6 μm.

(4) Provision of Spreading Layer

A membrane filter having a mean diameter of 3 μm (Microfilter FM-300, trade name, produced by Fuji Photo Film Co., Ltd., Japan) was impregnated with a 0.2% aqueous polyoxyethylene p-isooctylphenyl ether solution to produce a hydrophilic filter.

The surface of the diffusion-preventive layer prepared as above was wetted with a 0.2% aqueous polyoxyethylene p-isooctylphenyl ether solution. Then the hydrophilic membrane filter was fixed onto the surface of the diffusion-preventive layer under pressure and finally dried.

B. Measurement of Cholesterol

Onto the spreading layer of the analytical element (analytical film) as prepared above was spotted 10 μl. of a cholesterol standard liquid containing cholesterol in a variety of density. The temperature was kept at 37° C. to perform hydrolysis reaction. The progress of hydrolysis reaction was observed by measuring the reflective optical density of the color reaction layer at the lapse of 6 min., using a Maccbeth reflection densitometer. The results are set forth in Table 5.

COMPARISON EXAMPLE 4

A. Preparation of Analytical Element for Measurement of Cholesterol (1) Preparation of Coating Solution for Forming Color Reaction Layer The procedure of Example 1 was repeated except that 5 g. of methyl vinyl ether-maleic anhydride copolymer (inherent viscosity[η]=0.1-0.5) was dissolved in 100 ml. of water to prepare a binder solution. To the binder solution were added a color-forming compound (1,7-dihydroxynaphthalene and 4-aminoantipyrin) and peroxidase to prepare a coating solution for forming a color reaction layer.

(2) Formation of Color Reaction Layer

On the same PET film as in Example 1 was coated the coating solution prepared in the above-mentioned procedure (1), and dried at 50° C. by air to form a color reaction layer of 10 μm thick. After dried, a great amount of crystals precipitated over the surfece of the color reaction layer.

Then, a diffusion-preventive layer and a spreading layer were formed on the color reaction layer in the same manner as in Example 4 to prepare a multilayer analytical element.

B. Measurement of Cholesterol Activity

The analytical element (analytical film) prepared as above was evaluated on the cholesterol activity in the same manner as in Example 4. The hydrolysis reaction caused by a cholesterol standard liquid of various density having been applied to the analytical element was observed by measuring the reflective optical density of the color reaction layer at the lapse of 6 min. The results are set forth in Table 5.

TABLE 5

| Concentration of Standard Liquid (mg/dl.) | Reflective Optical Density of Color Reaction Layer | |
|---|---|---|
| | Example 4 | Com. Example 4 |
| 50 | 0.24 | 0.24 |
| 100 | 0.30 | 0.30 |
| 200 | 0.38 | 0.29 |
| 500 | 0.73 | 0.29 |

What is claimed is:

1. An analytical element having at least one reagent layer comprising a color-forming reagent which forms a color in the presence of an analyte and a hydrophilic binder wherein a portion or all of the binder is a polymer or copolymer containing a repeating unit represented by the formula

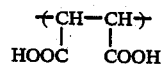 (I)

wherein at least a portion of the carboxyl groups in the repeating unit represented by formula (I), have a nonionic group containing a repeating unit represented by formula (II) attached to the carboxyl group through an ester linkage:

 (II).

2. The analytical element as claimed in claim 1, in which said nonionic group has the formula (III):

 (III)

in which R is an alkyl group having 2-22 carbon atoms, an aryl group containing substituent of an alkyl group of 4-12 carbon atoms, an alkylcarbonyloxy group containing an alkyl group of 9-19 carbon atoms, or a sorbitane or sorbitol residue having a hydroxyl group esterified with a carboxylic acid of 2-22 carbon atoms; and n is an integer from 2-40.

3. The analytical element as claimed in claim 1, in which said color-forming reagent comprises oxidoreductase and a color-forming compound capable of forming a dye under the action of a reaction product produced by reaction of an introduced analyte and the oxidoreductase.

4. The analytical element as claimed in claim 1 which is in the form of a multilayer analytical element for quantitative analysis of an analyte, comprising in this order, a spreading layer, a reagent layer and a transparent support which are superposed.

5. The analytical element as claimed in claim 4, in which said analyte is glucose, cholesterol, triglyceride or uric acid.

6. The analytical element as claimed in claim 4, in which said analyte is amylase.

7. The analytical element as claimed in claim 1 in which said copolymer contains said repeating unit of formula (I) and a monomer unit selected from the group consisting of methyl acrylate, ethyl acrylate, propyl acrylate, butyl acrylate, pentyl acrylate, hydroxyethyl acrylate, methyl vinyl ether, ethyl vinyl ether, propyl vinyl ether, butyl vinyl ether, styrene, and p-hydroxystyrene.

8. A multilayer analytical element for analysis of amylase comprising a diazonium color-forming layer containing a diazonium compound and a binder, and a coupler substrate layer provided on the diazonium color-forming layer, in which at least a portion or all of said binder is a polymer containing a repeating unit represented by formula (I)

wherein at least a portion of the carboxyl groups in the repeating unit represented by formula (I), have a nonionic group containing a repeating unit represented by formula (II) attached to the carboxyl group through an ester linkage:

* * * * *